US009439655B2

(12) United States Patent
Cosgrove et al.

(10) Patent No.: US 9,439,655 B2
(45) Date of Patent: Sep. 13, 2016

(54) SURGICAL SAGITTAL SAW AND BLADE CARTRIDGE, THE BLADE CARTRIDGE HAVING REINFORCING RIBS INTEGRAL WITH THE BLADE BAR

(71) Applicant: Stryker Corporation, Kalamazoo, MI (US)

(72) Inventors: Liam Cosgrove, County Clare (IE); James G. Walen, Kalamazoo, MI (US); Frank White, County Galway (IE)

(73) Assignee: STRYKER IRELAND LTD., Carrigtwohill (IE)

( * ) Notice: Subject to any disclaimer, the term of this patent is extended or adjusted under 35 U.S.C. 154(b) by 154 days.

(21) Appl. No.: 14/163,092

(22) Filed: Jan. 24, 2014

(65) Prior Publication Data
US 2014/0163558 A1 Jun. 12, 2014

Related U.S. Application Data

(63) Continuation of application No. PCT/US2012/048216, filed on Jul. 26, 2012.

(60) Provisional application No. 61/512,015, filed on Jul. 27, 2011.

(51) Int. Cl.
*A61B 17/14* (2006.01)
*A61B 17/32* (2006.01)
*A61B 17/00* (2006.01)

(52) U.S. Cl.
CPC ............. *A61B 17/141* (2013.01); *A61B 17/14* (2013.01); *A61B 17/320068* (2013.01); *A61B 2017/00734* (2013.01)

(58) Field of Classification Search
CPC ..... B26B 11/00; A61B 17/14; A61B 17/141; A61B 17/148
USPC .......... 606/82–85, 86 R, 167–174, 176, 178; 30/166.3, 392–394, 348, 208–210, 351
See application file for complete search history.

(56) References Cited

U.S. PATENT DOCUMENTS 2,854,981 A * 10/1958 Morrison ............... A61B 17/14
606/178
4,619,045 A * 10/1986 Mayer .................... A01G 3/053
30/216

(Continued)

FOREIGN PATENT DOCUMENTS

BR PI0615642 A2 * 12/2012
CN 101361670 A 2/2009

(Continued)

OTHER PUBLICATIONS

"ISA Search Report & Written Opinion" for PCT/US2012/048216, Nov. 2012.

*Primary Examiner* — Jason Daniel Prone

(57) ABSTRACT

A surgical sagittal and a saw blade cartridge. The saw has a head to which the blade cartridge is releasably mounted and a clamping assembly that releasably hold the cartridge to the head. The blade cartridge includes a blade bar, a blade head mounted to the bar and at least one drive rod that actuates the blade head. A rib projects from the blade bar to stiffen the cartridge. The rib extends over the blade bar so as to extend both proximally and distally relative to where the clamp assembly bears against the blade bar. The rib reduces skiving of the cartridge when a load is applied to either the top or bottom surface of the blade bar.

27 Claims, 5 Drawing Sheets

(56) References Cited

U.S. PATENT DOCUMENTS

| | | | |
|---|---|---|---|
| 4,941,466 A * | 7/1990 | Romano | A61B 17/1642 606/80 |
| 5,122,142 A * | 6/1992 | Pascaloff | A61B 17/14 606/171 |
| 5,201,749 A * | 4/1993 | Sachse | A61B 17/14 30/393 |
| D343,247 S * | 1/1994 | Walen | D24/146 |
| 5,735,866 A * | 4/1998 | Adams | A61B 17/14 606/178 |
| 5,846,244 A * | 12/1998 | Cripe | A61B 17/14 606/176 |
| 5,897,570 A * | 4/1999 | Palleva | A61B 17/1637 30/392 |
| 6,960,894 B2 * | 11/2005 | Carusillo | A61B 17/14 318/400.01 |
| 7,497,860 B2 | 3/2009 | Carusillo et al. | |
| 7,704,254 B2 * | 4/2010 | Walen | A61B 17/14 606/82 |
| 8,323,285 B2 * | 12/2012 | Walen | A61B 17/14 606/82 |
| 8,348,951 B2 * | 1/2013 | Walen | A61B 17/14 606/82 |
| 8,444,647 B2 * | 5/2013 | Walen | A61B 17/14 606/82 |
| 8,672,943 B2 * | 3/2014 | Fisher | A61B 17/14 606/82 |
| 8,696,673 B2 * | 4/2014 | Walen | A61B 17/14 606/82 |
| 8,966,772 B2 * | 3/2015 | Legrand | A61B 17/14 606/176 |
| 9,060,783 B2 * | 6/2015 | Walen | A61B 17/14 30/394 |
| 2006/0218796 A1 * | 10/2006 | Heinzelmann | A01G 3/053 30/276 |
| 2007/0083209 A1 * | 4/2007 | Schenberger | A61B 17/14 606/82 |
| 2010/0064525 A1 | 3/2010 | Walen et al. | |
| 2010/0292701 A1 | 11/2010 | Fisher et al. | |
| 2012/0289963 A1 * | 11/2012 | Legrand | A61B 17/14 606/79 |
| 2013/0060252 A1 * | 3/2013 | Walen | A61B 17/14 606/82 |
| 2014/0088600 A1 * | 3/2014 | Carusillo | A61B 17/14 606/82 |
| 2015/0282814 A1 * | 10/2015 | Walen | A61B 17/14 606/82 |

FOREIGN PATENT DOCUMENTS

| | | | |
|---|---|---|---|
| DE | 10 2004 028691 A1 | | 12/2005 |
| EP | 2319432 A1 | * | 5/2011 |
| EP | 2457520 A1 | * | 5/2012 |
| EP | 2520234 A1 | * | 11/2012 |
| KR | 20080059191 A | * | 6/2008 |
| KR | 20120112804 A | * | 10/2012 |
| KR | 20130049832 A | * | 5/2013 |
| WO | WO 2007030793 A3 | * | 8/2007 |
| WO | WO 2013016472 A1 | * | 1/2013 |

* cited by examiner

SURGICAL SAGITTAL SAW AND BLADE CARTRIDGE, THE BLADE CARTRIDGE HAVING REINFORCING RIBS INTEGRAL WITH THE BLADE BAR

RELATIONSHIP TO EARLIER FILED APPLICATION

This application is a continuation of PCT Pat. App. No. PCT/US2012/048216 filed 26 Jul. 2012. PCT Pat. App. No. PCT/US2012/048216 is a nonprovisional of U.S. Prov. Pat. App. No. 61/512,015 filed 27 Jul. 2011. The above-listed applications from which this application claims priority are now explicitly incorporated herein by reference.

FIELD OF THE INVENTION

This application relates generally to a surgical sagittal saw and blade cartridge. The saw and blade cartridge of this assembly includes ribs integral with the cartridge that inhibit flexing of the cartridge.

BACKGROUND OF THE INVENTION

A sagittal saw is a powered surgical tool used in an orthopedic surgical procedure. A sagittal saw generally includes a handpiece that houses a motor and the complementary control circuit that regulates actuation of the motor. Extending forward, distally, from the handpiece is a head. Internal to the head is an oscillating shaft. Removably attached to the oscillating shaft is a saw blade. The exposed distal front edge of the blade is formed with teeth. The teeth cut the tissue against which the blade is applied. A drive mechanism internal to the housing generates power. This power actuates the oscillating shaft so that the shaft and the attached blade move in a back-and-forth pattern in which the blade is aligned. When the saw is so actuated, the blade teeth move in a right/left/right/left pattern against the tissue against which they are applied. Due to the forward pressure applied by the surgeon holding the saw, the teeth cut and separate the hard tissue against which the blade is applied.

A sagittal saw is often used in an orthopedic surgical procedure to selectively remove bone. One particular type of orthopedic surgical procedure in which the saw is used is a joint replacement procedure. As implied by the name, in this type of procedure, the surgeon resects the bone between the joints in the patient and substitutes an artificial joint. In an orthopedic surgical procedure it is important to ensure that, when the section to be resected is separated from the remaining bone, the section is removed along precise lines. This precision is important because the substitute joint typically has a component designed to precisely fit in the space left by the cut line of the bone left in place.

To ensure the cuts are properly formed in the bone, the surgeon typically first mounts a resection guide, sometimes called a cutting guide or a jig, to the bone adjacent the location at which the cut is to be made. One type of resection guide is in the form of a block with a precisely shaped set of slots. The slots define the lines along which the bone is to be cut. The surgeon removes the bone by sequentially inserting the saw blade in the slots. Once the blade is inserted in a slot, the saw is actuated. This arrangement enables the surgeon to cut the bone along the precisely defined lines.

Many standard sagittal saws and their complementary blades adequately cut the bone against which the blades are applied. However, some limitations are associated with these assemblies. Many commercially available sagittal saws are provided with planar blades that oscillate. The blade inevitably rubs against the surfaces resection guide material that defines the slot(s) in which the blade is inserted. This repetitive contact wears away the slot-defining material. Eventually the slot may become so wide that it no longer precisely defines the intended cut line. Once a resection guide is so worn, it needs to be replaced. It should similarly be appreciated that, the repeated abutment of the saw blade against the resection guide can cause the guide to move. If an accurate cut is desired this movement is, at a minimum, undesirable. Moreover, the wearing of the material forming the resection guide generates a fine dust of material. Some of this dust inevitably settles on the surgical site at which the procedure is being performed. Consequently, during the procedure, the surgical personnel are required to spend an appreciable amount of time flushing the site to remove this dust. Having to repeatedly perform this process runs counter to one of the primary goals when performing surgery; that one should perform the procedure as quickly as possible to minimize the time that both the exposed tissue is open to infection and the patient is held under anesthesia. As discussed above, the oscillating blade of a conventional sagittal saw blade will repeatedly gall the surfaces of the cutting guide forming the slot in which the blade is inserted. One further disadvantage of this blade galling it consumes power. Many sagittal saws are battery powered. The power expended overcoming the blade galling-induced friction reduces the overall amount of power available to actuate the saw. This reduces the overall amount of time the battery, on a single charge, is able to power the saw.

Moreover, as a consequence of the saw blade galling against a surface of the resection guide, then pulling away from this surface, there is some jerking of the blade. The jerking motion is transferred from the blade through the handpiece into the hand of the surgeon holding the saw. Consequently, the surgeon must exert some muscle control to hold the handpiece steady when he/she is exposed to this jerking motion. Also, an inevitable result of the back-and-forth motion of the blade, the sagittal saw itself vibrates. Again, the surgeon is required to engage in some conscious or unconscious physical effort to hold the saw steady when it vibrates. Over time, having to so hold the saw to overcome this vibration can be significantly mentally and physically fatiguing.

The Applicant's Assignee's U.S. Pat. No. 7,497,860, SURGICAL SAGITTAL SAW INCLUDING A HANDPIECE AND A REMOVABLE BLADE ASSEMBLY, THE BLADE ASSEMBLY INCLUDING A GUIDE BAR, A BLADE HEAD CAPABLE OF OSCILLATORY MOVEMENT AND DRIVE ROD FOR ACTUATING THE BLADE HEAD and U.S. Pat. No. 7,704,254, SURGICAL SAGITTAL SAW WITH INDEXING HEAD AND TOOL-LESS BLADE COUPLING ASSEMBLY FOR ACTUATING AN OSCILLATING TIP SAW BLADE, both incorporated herein by reference, disclose a saw and complementary saw blade that essentially eliminate the limitations described above. The blade assemblies of these inventions each includes a bar to which a blade head is pivotally mounted. Drive rods disposed in the bar extend proximally rearward. The blade bar is removably attached to a head that is part of that is part of the saw of this invention. The drive rods are coupled to an oscillating shaft integral with saw head. When the saw of this invention is actuated, the oscillating shaft moves back and forth. This movement, in turn, causes the drive rods to reciprocate. The drive rods thus oscillate the blade head around the pivot point against which it is mounted.

The above saw and blade assembly are designed so that, only the distally located blade head oscillates. The blade bar remains static. This eliminates many of the problems that otherwise occur if the whole of the blade moves back and forth.

The blade assembly of the above patents works well. However, the assembly has the potential of flexing. Sometimes this flexing is referred to as skiving. Skiving is especially known to occur when the blade head is pressed against the tissue the blade assembly is to cut at an angle that is spaced from the normal angle to the tissue. This skiving, if exceeding a threshold can, in some circumstances be undesirable.

SUMMARY OF THE INVENTION

This invention is directed to a new saw and blade cartridge assembly.

The blade cartridge of this invention includes a static bar formed with one or more stiffening ribs. The ribs are positioned relative to the saw to minimizing the flexing, the skiving, of the cartridge. More particularly, the ribs are positioned relative to the components of the saw to both inhibit flexing of the cartridge and not restrict the ability of the surgeon to position the saw in a resection guide.

In some versions of the invention, the stiffing ribs extend over the portion of the blade bar that seats against the saw to which the cartridge is mounted. In some preferred versions of the invention, the stiffening ribs do not extend forward of the portion of the most proximal portion of the saw to which the cartridge is mounted.

In many versions of the invention, a clamping assembly releasably holds the blade bar to the saw. The clamping assembly engages the blade bar at a location forward of the distal end of the bar and proximal to the distal end of the portion of the saw to which the blade bar is mounted. In these versions of the invention, the stiffening rib extends at least forward of and/or rearward of where the blade bar is clamped to the saw.

BRIEF DESCRIPTION OF THE DRAWINGS

The invention is pointed out with particularity in the claims. The above and further features and advantages of the invention are better understood from the following Detailed Description taken in conjunction with the accompanying drawings in which:

DETAILED DESCRIPTION

Figure 1:
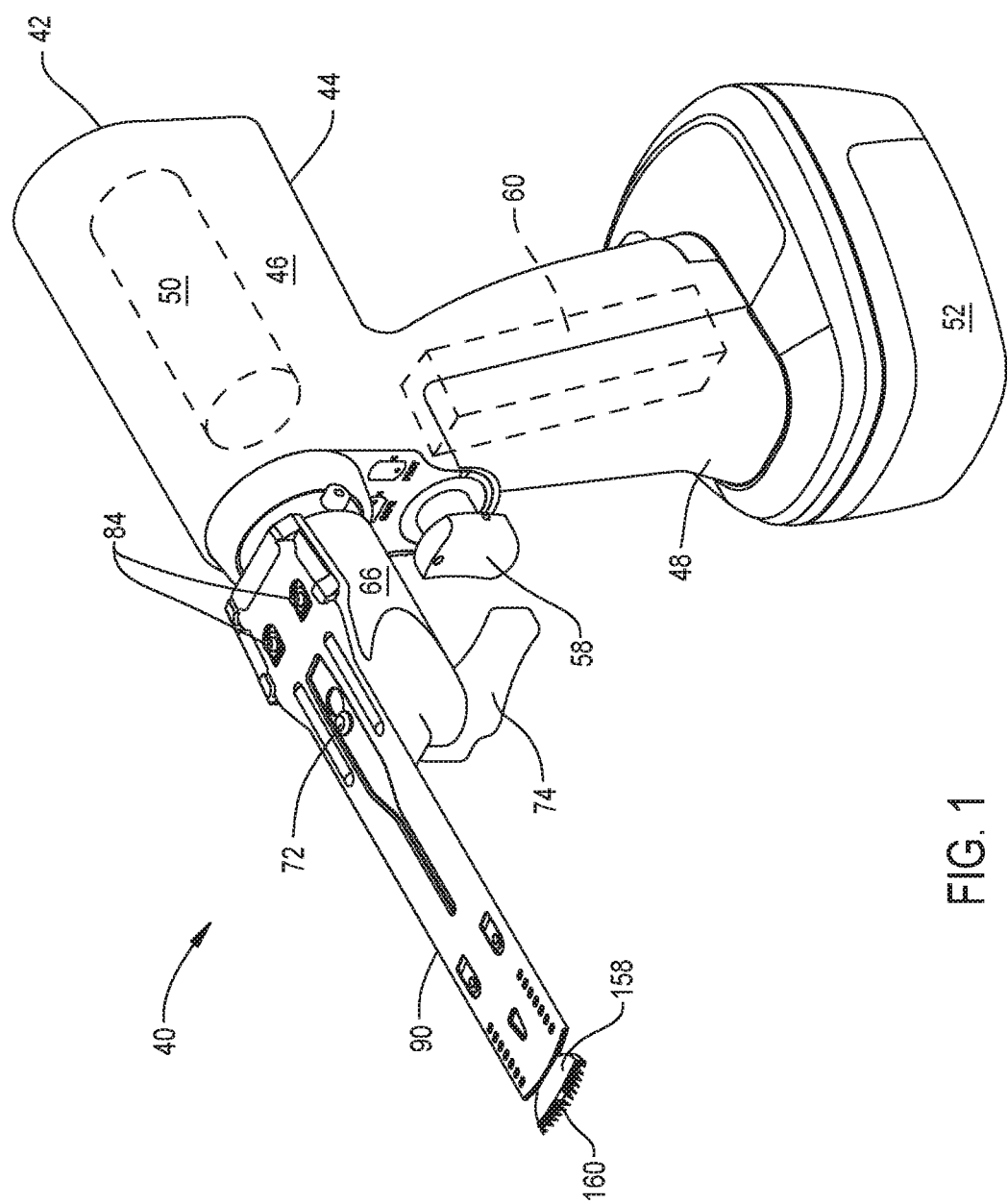
FIG. 1 is a saw and blade cartridge assembly of this invention.

FIG. 1 depicts a saw and blade cartridge assembly 40 of this invention. Assembly 40 includes a saw 42 and a blade cartridge 90 that is attached to the saw. Saw 42 includes a housing 44. The housing 44 has an elongated, top-located barrel section 46. A pistol-grip shaped handle 48, also part of housing 44, extends downwardly from barrel section 46. A motor 50, depicted as a phantom cylinder in FIG. 1, is disposed inside the housing barrel section 46. In some versions of the invention, motor 50 is a brushless, sensorless DC motor. This is exemplary, not limiting. In other versions of the invention, the motor 50 may be a DC motor with brushes and/or sensors, an AC driven motor or a motor that is pneumatically or hydraulically driven. In the illustrated version of the invention, saw 42 is a cordless power tool. A battery 52 removably attached to the butt end of handle 48 contains a charge for energizing the motor. Again, it should be understood that the invention is not so limited. In alternative versions of the invention, a power cord, an air line or a hydraulic line is connected to the housing 44 for providing the power needed to actuate the motor 50.

A trigger 58 extends distally forward from the front end of housing handle 48 below barrel 46. ("Distal", it shall be understood, means toward the surgical site to which the handpiece 42 is directed. "Proximal" means away from the surgical site.) The trigger 58 is moveably mounted to the saw housing 44. A control circuit 60, depicted as a phantom rectangle, monitors actuation of the trigger 58. Based on the extent to which the trigger 58 is actuated, the control circuit 60 selectively energizes motor 50 to cause a motor rotor 64, (FIG. 2) to rotate at the desired speed. The structure of the control circuit is outside the scope of this invention.

Figure 2:
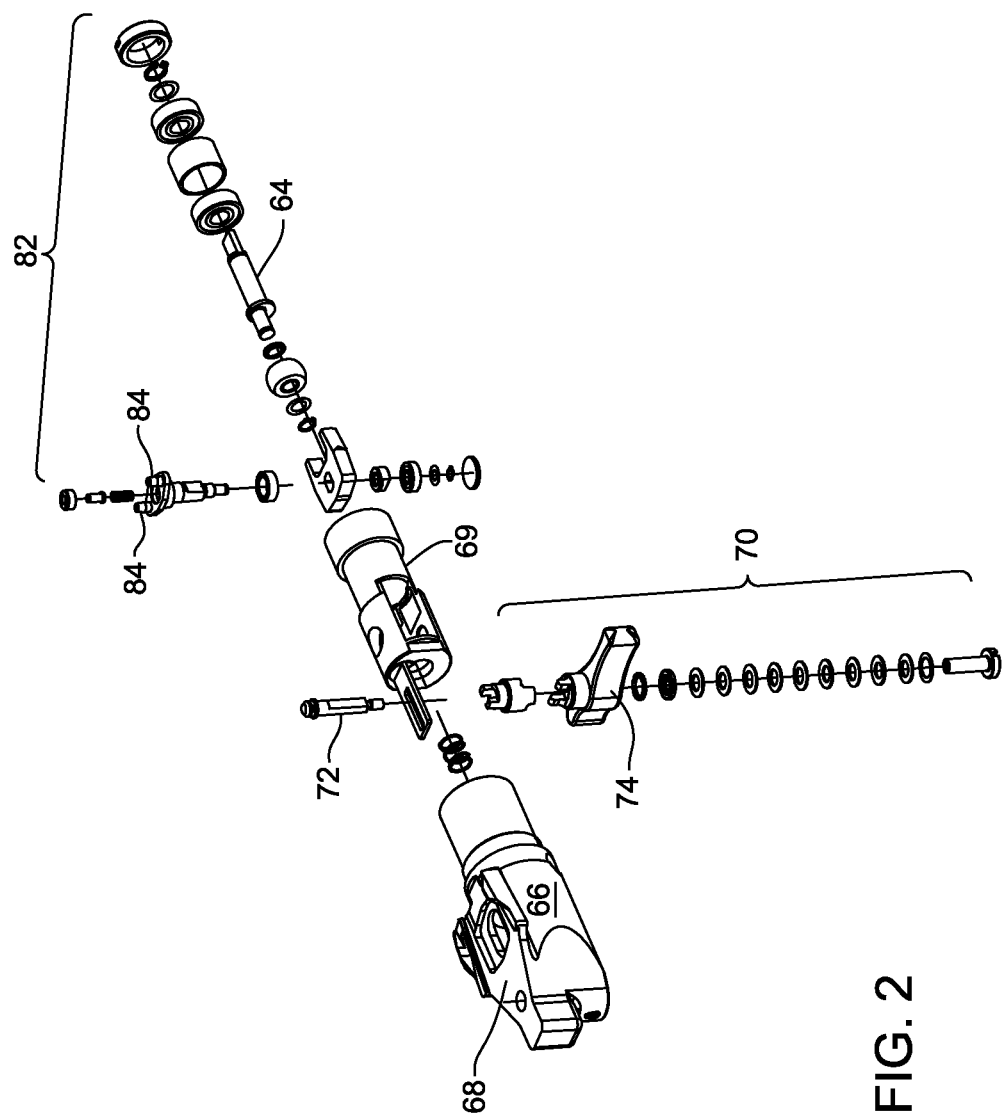
FIG. 2 is an exploded view of the sub assemblies internal to the head of the saw.

A head 66, seen in FIGS. 1 and 2, extends forward from the barrel 46. Head 66 has opposed proximal and distal ends and a planer top surface 68. The proximal end of the blade cartridge 90 is seated on head top surface 68. Disposed inside the head 66 is an inner housing 69. Two sub-assemblies that are mounted to the head 66 and inner housing 69 are a blade lock assembly 70 and a drive assembly 82.

While not depicted, it should be understood that often head 66 is rotationally mounted to housing 44. For example, in many versions of the invention, the head 66 can rotate around an extension of the longitudinal axis that extends through housing barrel section 46. This allows the practitioner some ability to set the plane in which blade cartridge 90 is disposed relative to an axis that extends through the saw 40.

The blade lock assembly 70 includes a coupling rod 72 that extends above head top surface 68. The blade lock assembly 70 moves the coupling rod 72 to set the height of the head of the rod 72 relative to the saw head top surface 68. The position of the coupling rod 72 is established by a manually set lock nut 74, also part of lock assembly 70. Specifically, the coupling rod 72 is moved between a first state, a load state, that allows blade cartridge 90 to be fitted to or removed from the head 66 and a second state, a run state. In the run state, coupling rod 72 releasably holds the blade cartridge 90 to saw head 66. More specifically, the coupling rod 72 bears against the below described cartridge blade bar 92 so that the cartridge is clamped between saw head surface 68 and the coupling rod.

Drive assembly 82 includes two drive pins 84. The drive pins 84 project above head top surface 68. The drive assembly 82 is connected to the motor rotor 64. Drive assembly 82 is configured to, upon actuation of the motor 50 and rotation of the rotor 64, oscillate the drive pins 84 in opposed arcs. The oscillation of the drive pins 84 results in the pivoting of the below discussed blade head 94 which is part of the blade cartridge 90.

Blade cartridge 90, now described by reference to FIGS. 3 and 4, includes a static blade bar 92 to which a blade head 94 is pivotally mounted. Drive rods 96 that extend distally from the blade head 94 connect the blade head to the saw drive pins 84. The drive rods 96 transfer the oscillatory motion of the saw drive pins 84 to the blade head 94.

The blade bar 92 includes lower and upper plates 102 and 104, respectively. Both plates 102 and 104 are generally planar. The lower plate 102 has a proximally located base 108. Base 108 is generally in the form of a trapezoid wherein the opposed side edges are symmetric and taper outwardly from the proximal end of the plate 102. The side edges of the base 108 project out a short distance between the more distally located side edges of the rest of the plate 102. The plate 102 is further formed to have two openings 112 located in the base 108. Each opening 112 is the form of a truncated oval wherein the curved edge of the opening is proximally directed and at the distal end, the opening 112 has a straight edge. The major axes of openings 112 are parallel to and symmetrically located around the longitudinal axis of the plate 102. Lower plate 102 is further formed to have two bosses 113. Bosses 113 project upwardly from plate base 108. More particularly, the bosses 113 extend upwardly from opposed distal portions of the plate boss 113 that are located outwardly of the more narrow width main section of the plate 102.

Distally forward of base 108 and openings 112, the lower plate 102 is formed to have a keyhole shaped opening 114. The plate 102 is shaped so that opening 114 is centered on the plate longitudinal axis. The narrow width section of opening 114 is the most proximally located portion of the opening. Proximal to the distal end of the plate 102, the lower plate 102 is formed to have two additional openings 116. Each opening 116 is in the form of a truncated oval and is longitudinally aligned with one of the openings 112. Each opening 116 is a mirror to the companion opening 112. The curved end of each opening 116 is distally directed; at the proximal end, the opening 116 has a straight edge.

Lower plate 102 is further formed to have a cylindrical boss 117 that extends upwardly from the inner face of the plate. Boss 117 is located between openings 116. Forward of openings 116, lower plate is further formed to have plural openings 118 and plural openings 120. Openings 118 are oval shaped openings located along the outer sides of the plate 102. There are two rows of openings 118, one located on each side of the plate. Lower plate 102 is shaped so that the major axes of openings 118 are perpendicular to the longitudinal axis of the plate. Openings 120 are also oval shaped. There are two openings 120. The openings 120 are disposed between the rows of openings 118.

Figure 5:
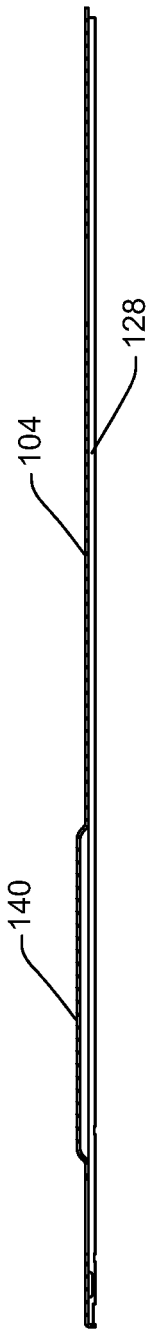
FIG. 5 is a cross sectional view of the upper plate of the blade cartridge.
Figure 4:
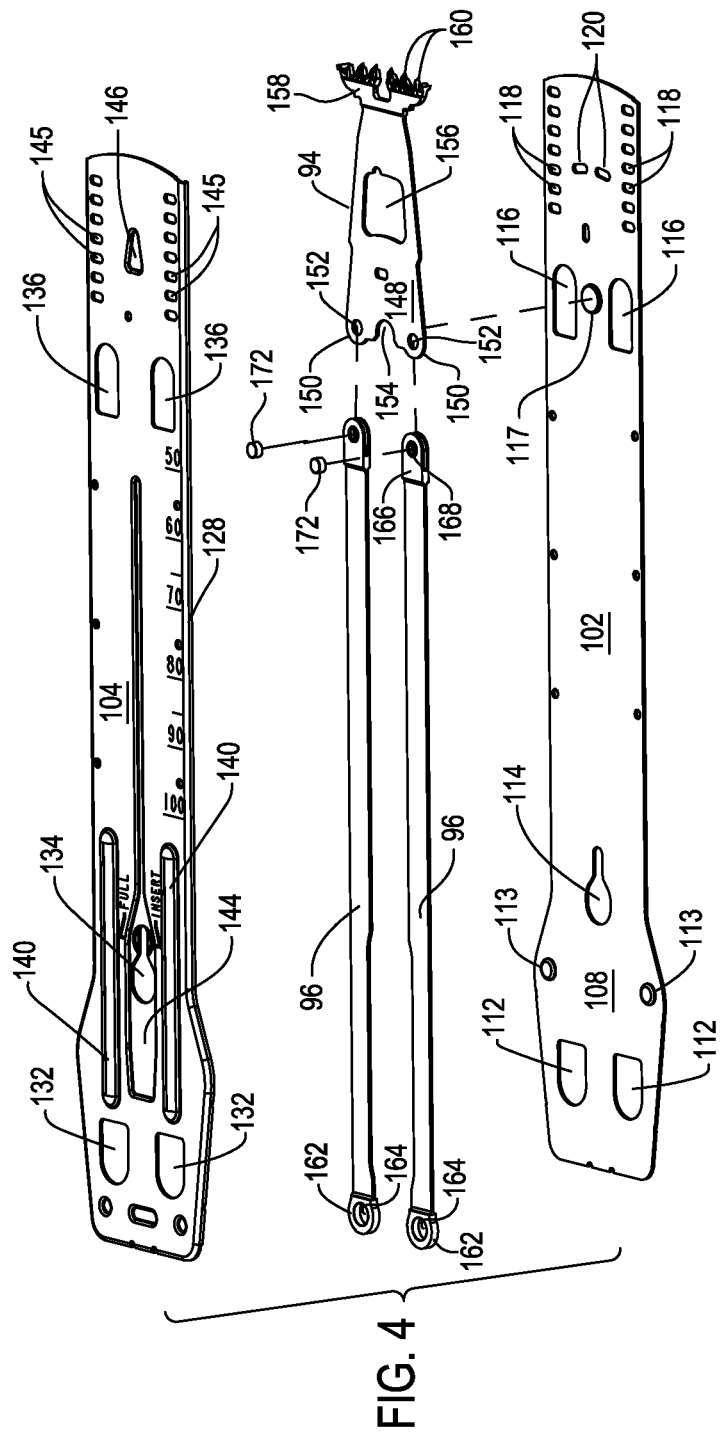
FIG. 4 is a exploded view of the blade cartridge of this invention.

The upper plate 104, now described by reference to FIGS. 4 and 5, is shaped to have the same general perimeter profile of the lower plate 102; the description of this profile is not repeated. Upper plate 104 is further formed to have a lip 128 that extends downwardly from the edges of the plate. Collectively, the plates 102 and 104 are dimensioned so that when the upper plate 104 is disposed over the lower plate 102, the upper plate lip 128 extends around the adjacent edges of the lower plate 102. The upper plate 104 is formed so that lip 128 extends around the proximal end of the lower 102 plate and the opposed longitudinally extending side edges of the lower plate 102. Thus, upon assembly, blade bar 92 has a distal end opening between the lower plate 102 and the upper plate 104 (opening not identified).

Bar upper plate 104 is further formed to have two openings 132, an opening 134 and two openings 136. Each opening 132 has the same shape and orientation as the lower plate openings 112. Opening 134 has the same shape and orientation as lower plate opening 114. Openings 136 have the same shape and orientation as openings 116. When blade cartridge 90 is assembled, plates 102 and 104 are welded together. The plate openings are located so that, at the conclusion of the cartridge assembly process: each upper plate opening 132 is in registration over one of the lower plate openings 112; upper plate opening 134 is in registration over the lower plate opening 114; and; each upper plate opening 136 is in registration over one of the lower plate openings 116.

Bar upper plate 104 while generally planar, is formed to have two ribs 140. The plate 104 is formed so that the ribs 140 have longitudinal axes that are parallel to and symmetrically located relative to the longitudinal axis of the plate. Each rib 140 is located forward of and is longitudinally aligned with a separate one of the openings 132. More specifically, each rib 140 extends forward from a location approximately 0.2 cm forward of the associated opening 132 and has a length of approximately 4.0 cm. Each rib 140 is thus partially located in and extends forward of the base of the upper plate. Each rib 140 projects approximately 0.1 cm above the face of the plate 104. Plate 104 has a thickness of approximately 0.04 cm. The sides and opposed ends of the ribs 140 are rounded.

Figure 3:
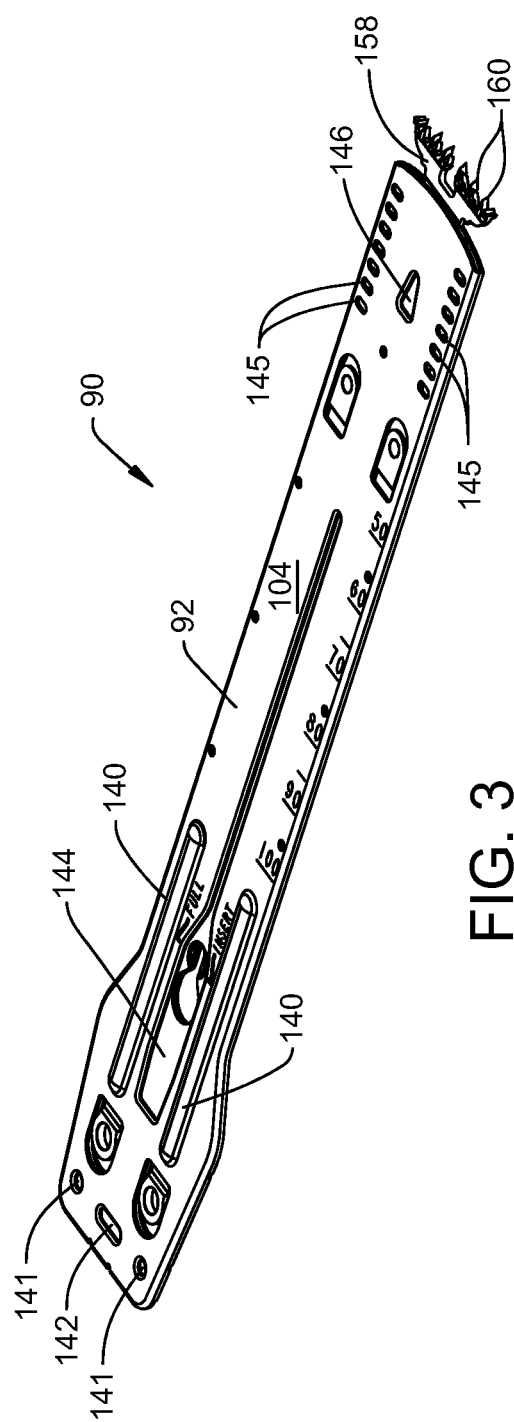
FIG. 3 is a perspective view of the blade cartridge of this invention.

Immediately forward of the proximal end of the plate 104, the upper plate has two gussets 141 and a single gusset 142, identified in FIG. 3. Gussets 141 and 142 are located proximal to openings 132. Gussets 141 are circularly shaped and symmetrically located relative to the longitudinal axis of the plate 104. Each gusset 141 is located outwardly of the longitudinal axis of the adjacent opening 132. Gusset 142 is oval shaped. The minor axis across gusset 142 is centered on the longitudinal axis of the plate 104. The centers of gussets 141 and longitudinal axis of gusset 142 are linearly aligned. Upper plate 104 also has two gussets 144 and 146 that are recessed relative to the face of the plate. Both gussets 144 and 146 are centered on the longitudinal axis of the plate 104. Gusset 144 extends forward from a location slightly forward of the proximal end of ribs 140. Gusset 144 extends to a location slightly proximal to the proximal ends of openings 136. The section of gusset 144 between the ribs 140 is relatively wide in width. Opening 134 is formed in this portion of the gusset 144. Forward of opening 134 gusset 144 tapers inwardly. From a location slightly proximal to the distal ends of the ribs 140 to the distal end of the gusset 144 the gusset 144 has a constant and narrow width. Gusset 146 is triangularly shaped and located forward of plate openings 136. Ribs 140 and gussets 144 and 146 are typically formed by a stamping process.

Slightly proximal to the distal end of the upper plate 104, the plate is formed to have two rows of oval shaped openings 145. Each row of openings 145 is located adjacent one side of the plate 104. Openings 145 are thus located on the opposed sides of gusset 146. Openings 145, like lower plate openings 118, are arranged so that their major axes are perpendicular to the longitudinal axis of cartridge bar 92.

The blade head 94 includes a base 148 with a relatively thin thickness. The blade head base 148 is dimensioned to oscillate in the gap between lower and upper plates 102 and 104, respectively. In one version of the invention, the blade head base 148 has a thickness approximately 0.002 cm less than the width of the gap between the opposed faces of the lower and upper plates 102 and 104, respectively. Blade head base 148 has a wide proximal end and tapers to a narrower distal end. The proximal end of base 148 is further formed to have, adjacent each side edge a foot 150. Each foot 150 is arcuately shaped. Through holes 152 are further formed in blade head base 148 immediately forward of the proximal end. Each through hole 152 is centered on the axis around which the surrounding foot 150 is centered. The distal end of the blade head base 148 blade head base is further formed to define a concave semi-circular notch 154. Notch 154 is centered along the longitudinal axis of the blade head 94. Blade head base 148 is further formed to define a through window 156. Window 156 is positioned so that when the blade 52 is assembled, upper plate gusset 146 extends through the window.

Formed integral with the base 148, blade 94 has a crown 158. Crown 158 has a thickness greater than that of the associated base 148. Blade teeth 160 are formed in the crown 158. More particularly the blade head crown 158 is formed so that the kerf cut by the teeth 160 is sufficiently wide to allow the insertion of the blade bar 92 into the kerf. The exact geometry of the blade head crown 158 is a function of the particular kerf geometry and not otherwise relevant to this invention. (There are some differences between the crown of FIG. 1 and the crown of FIGS. 3 and 4. These differences are not relevant to the current invention.)

Drive rods 96 are disposed between the blade bar lower and upper plates 102 and 104, respectively. Each drive rod 96 is in the form of an elongated flat strip of metal. The drive rods 96 are formed so that, at the proximal end of each rod, there is a circular foot 162. Each foot 162 has a thickness that is greater than that distally extended elongated portion of the rod 96, In some versions of the invention, the basic thickness of the drive rod 96 is approximately 0.38 mm; foot 162 has a thickness of approximately 1.1 mm. Each foot 162 is formed to have a center located through hole 164. Through holes 164 are dimensioned to receive saw drive pins 84.

Fingers 166 and pins 172 pivotally connect each drive rod 96 to the blade head 94. Two parallel overlapping fingers 166 extend forward from the opposed distal end surfaces of each drive rod 96. Fingers 166 are thus located outwardly of the exposed major surfaces of the drive rods 96. The gap between the fingers 166 is such that the blade head base foot 152 can slip fit between the fingers. Each finger 166 is formed with a hole 168. Finger holes 168 are formed so that the holes 168 of each pair of fingers 166 overlap in the section of the fingers that extend forward beyond the drive rods 96. In the depicted version of the invention, fingers 166 are integrally formed with the drive rods 96.

Blade head 94 is fitted to the rest of the blade cartridge 90 so that each base foot 150 seats in the gap between a separate pair of fingers 166. When the blade head 94 is so positioned, each blade head hole 152 aligns with a separate pair of finger holes 168. A pin 172 is fitted in each set of aligned blade head and finger holes 152 and 168, respectively, to hold the drive rod 96 to the blade head 94. Each pin 172 is welded or otherwise secured to the opposed finger holes 168 in which the pin is seated.

Once the blade head and drive rod sub-assembly is fabricated, this sub assembly is placed against the inner surface of the lower plate 102. The blade head 94 is positioned so that the lower plate boss 117 seats in the blade head notch 154. Upper plate 104 is then seated over the lower plate 102, the blade head 94 and drive rods 96. More particularly the upper plate 104 is positioned so that the upper plate lip 128 seats around the outer perimeter of the lower plate 102. As a result of this arrangement, feet 162 at the proximal end of the drive rods 96 seat in lower and upper plate openings 112 and 132, respectively. Fingers 166 and pins 172 seat in lower and upper plate openings 116 and 136.

The blade head crown 158 projects forward of the plates 102 and 104. Plates 102 and 104 are then welded together to complete assembly of the blade cartridge 90.

Figure 6:
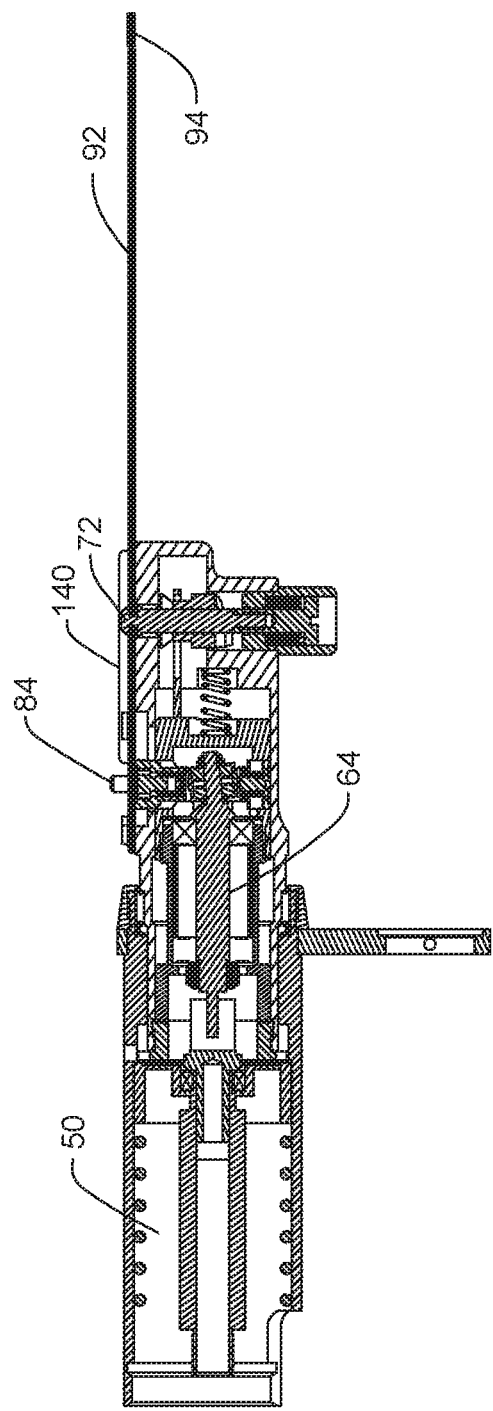
FIG. 6 is a cross sectional view depicting how the blade cartridge is releasably secured to the head of the saw.

Assembly 40 is prepared for use by attaching the blade cartridge 90 to the saw 42. Cartridge 90 is positioned so that the proximal portion of the cartridge lower plate 102 is disposed against saw head top surface 68. More specifically, the cartridge 90 is positioned so that the saw drive pins 84 seat in the holes 164 internal to the drive rod feet 162 as seen in FIGS. 1 and 6. Also, the cartridge 90 is positioned so that the coupling rod 72 extends through overlapping openings 114 and 136 in the cartridge bar 92. Lock knob 74 is then actuated to cause the lock assembly to press the coupling rod 72 downwardly, towards the saw head surface 68 and against the bar upper plate 104. The abutment of the coupling rod 72 against the cartridge 92 releasably holds the blade cartridge 90 to the saw 42. Saw 40 and blade 90 are in the run state.

In the described version of the invention, when the cartridge 90 is mounted to the saw 40, ribs 140 are located on the opposed sides of the coupling rod 72. Each rib 140 extends both proximally and distally along the cartridge relative to the coupling rod 72. Ribs 140 do not extend forward of the distal end of saw head 66. Ribs 140 thus are understood to terminate at a location proximal to the distal end of the blade bar 92. Thus in many versions of the invention, ribs 140 extend over the blade bar a distance less than 50% of the overall length of the bar.

Ribs 140 stiffen the cartridge bar 92 and, by extension, the whole of the cartridge 90. One such situation in which the ribs perform this stiffening is when a force is applied against bar lower plate 102. Without the presence of the ribs, the bar 92 has a tendency to flex upwardly forward of where the coupling rod 72 clamps the cartridge to the saw head 66. The sections of the ribs 140 located forward of the coupling rod 72 inhibit the flexing of the portion of the cartridge 90 disposed over the saw head 66. This substantially reduces upward flexing, skiving, of the cartridge 90 forward of the saw 40.

Alternatively an unopposed force may be applied against the bar upper plate 104. In the absence of the ribs, the blade bar 92 can become a lever that pivots around the distal edge of the saw head 66. This pivoting action works in opposition to the components of the coupling assembly 70 that hold the rod 72 against the blade bar. This force can cause a slight upward displacement of the coupling rod 72. This displacement is not enough to adversely affect the ability of the rod 72 to hold the cartridge 90 to the saw 42. However, this displacement of the coupling rod means that the portion of the cartridge 90 proximal to the distal end of the saw head 66 is able to engage in some movement away from head surface 68. This displacement of the proximal end of the blade bar 92 does not restrict the downward movement, the downward flexure or skiving, of the portion of the blade bar that extends forward of saw head 66.

Ribs 140 inhibit this upward flexure of the blade bar 92 both distal to and proximal to the coupling rod 72. The limiting of this flexure of the portion of the cartridge that is seated on the saw head surface 68 reduces the extent to which the portion of cartridge 90 that extends forward of the saw head is able to flex, skive, downwardly from the saw head 66.

Still another feature of this invention, is that ribs 140 do not extend distally forward of the distal end of the saw head 68. This ensures that the ribs do not inhibit the insertion of the cartridge in a resection guide.

It should be understood that the above is directed to just one embodiment of this invention. This invention may have features different from what has been described. For example, some versions of this invention may include only a single rib. These versions of the invention may be constructed so that the rib is relatively wide across. Still other versions of this invention may include three or more ribs.

Likewise, this invention is not limited to versions of the invention wherein the cartridge 90 has two drive rods 96. In alternative versions of the invention, the cartridge 90 may have a single drive rod 96 or three or more drive rods. In some alternative versions of the invention, the drive rod and blade head may be a single piece structure.

Likewise the saw may have different structural features that clamp the cartridge 90 to the saw head 68. These features may include a set of pins on opposed sides of the cartridge that press against the cartridge bar 92. An alternative locking mechanism may be a bar or rod that presses down against the cartridge bar 92. In many versions of these embodiments of the invention, the rib 140 or ribs extend both proximal to and forward of the saw clamping component. The cartridge 90 may have features other than an opening that engage these clamping components.

In some versions of the invention the at least one rib 140 may not extend upwardly from the blade bar 92. In these versions of the invention, the rib 140 may extend downwardly adjacent a side surface of the saw head 66. In these versions of the invention, the saw head 66 may have side surfaces that taper inwardly towards the most distally located front face of the head. Alternatively, in these versions of the invention, the saw head may be formed with one or more channels. When the blade bar with one or more downwardly extending ribs is fitted to the saw, each rib seats in a complementary channel.

Likewise there is no obligation that in all versions of the invention, the rib 140 or ribs extend both proximally rearward and distally forward from the saw clamping component. In most versions of the invention, the rib 140 or ribs do extend forward of the saw clamping component. This prevents the flexure of the cartridge forward of the saw head 68. Similarly, in some versions of the invention, the cartridge may have plural sets of ribs 140. The first set of ribs includes one or more ribs 140 that are extend forward of the saw clamping component. The second set of ribs 140 extend rearward of the saw clamping component. Depending on the structure of the saw 140, some or all of the ribs 140 of the second set of ribs may be longitudinally spaced from some or all of the ribs of the second set of ribs. Further in some versions of the invention, it may be desirable to shape the cartridge 90 so that at least one of the ribs 140 extends forward of the saw surface on which the cartridge is seated.

Therefore, it is an objection of the appending claims to cover all such variations and modifications that come within the true spirit and scope of this invention.

What is claimed is:

1. A sagittal saw and blade cartridge assembly, including:
    a saw having:
        a head with a surface, the surface having opposed proximal and distal ends;
        a lock assembly attached to said saw head that includes a clamping member mounted to said saw head that extends over the saw head surface at a location proximal to the distal end of the saw head surface and that is moveably mounted to said saw head so as to selectively bear against a blade bar disposed on the saw head surface so as to releasably hold the blade bar to the surface; and
        an oscillating drive assembly mounted to said head that has a drive member shaped to engage at least one blade cartridge drive rod, the oscillating drive assembly configured to receive a rotational movement and convert the rotational movement into movement that oscillates the said drive member; and
    a blade cartridge including:
        a blade bar that has opposed proximal and distal ends that is releasably attached to the surface of said saw head so as to be disposed between the surface and said lock assembly clamping member so that the clamping member can releasably hold said blade bar to the saw head surface;
        at least one rib that extends outwardly from an outer surface of said blade bar, said rib being located so that, when said blade bar is held to the surface of said saw head, said rib extends proximal to said lock assembly clamping member and distally forward of said clamping member and said at least one rib does not extend beyond the distal end of the saw head surface;
        a blade head having a base disposed in said blade bar adjacent the distal end of said blade bar and a crown that extends forward from said base so as to be located forward of the distal end of said blade bar, said crown having teeth and having a thickness greater than that of said blade head base, so that a kerf cut by said teeth is of sufficient width to accommodate the distal end of said blade bar; and
        at least one drive rod that is connected to said blade head base and extends from said blade head base towards the proximal end of the blade bar, said drive rod being configured for releasable attachment to said drive member of said saw oscillating drive assembly so that the actuation of said drive member results in reciprocation of said at least one drive rod which results in the oscillation of said blade head.

2. The surgical saw and blade cartridge assembly of claim 1, wherein said blade cartridge is formed so that said at least one rib extends outwardly away from said blade bar so that when said blade cartridge is mounted to said saw, said at least one rib extends outwardly away from the saw head surface.

3. The surgical saw and blade cartridge assembly of claim 1, wherein said blade cartridge is formed so that the at least one said rib is two said ribs and said ribs are located on opposed sides of said blade bar so that when said blade cartridge is attached to said saw, head, said ribs are located on opposed sides of said clamping member of said saw locking assembly.

4. The surgical saw and blade cartridge assembly of claim 1, wherein said at least one rib of said blade cartridge extends distally forward along said blade bar from a location that is distal to the proximal end said blade bar and proximally rearward of said clamping element of said saw lock assembly.

5. The surgical saw and blade cartridge assembly of claim 1, wherein said blade cartridge is further constructed so that:
    said blade head base is disposed in said blade bar to pivot around a static surface internal to said blade bar; and
    said at least one drive rod is two said drive rods internal to said blade bar, wherein said drive rods extend proximally from said blade head base on opposed sides of the static surface internal to said blade bar around which said blade head base pivots.

6. A sagittal saw and blade cartridge assembly, including:
    a saw having:
        a head having proximal and distal ends and a surface;

a lock assembly that includes a clamping member mounted to said saw head that extends over the saw head surface at a location proximal to the distal end of said saw head that is moveably mounted to said saw head so as to selectively bear against a bar disposed on the saw head surface so as to secure the bar to the surface; and an oscillating drive assembly mounted to said head that has a drive member shaped to engage at least one blade cartridge drive rod, the oscillating drive assembly configured to receive a rotational movement and convert the rotational movement into movement that oscillates the drive member; and a blade cartridge including:

a blade bar that has opposed proximal and distal ends, a length between the ends and that is releasably seated on the surface of said saw head so as to be disposed between the surface and said lock assembly clamping member so that said clamping member can releasably hold said blade bar to the saw head surface, said blade bar being formed with a first opening located distal to the proximal end of said blade bar through which, when said blade bar is seated on the surface of said head, said clamping member extends;

at least one rib that extends outwardly from an outer surface of said blade bar, said rib being located so that, when said blade bar is held to the surface of said blade bar, said at least one rib extends both proximally and distally away from the first opening in said blade bar and over said blade bar a distance less than one-half the length of said blade bar so as to terminate at a location proximal to the distal end of said blade bar;

a blade head having base disposed in said blade bar adjacent the distal end of said blade bar and a crown that extends forward from said base so as to be located forward of the distal end of said blade bar, said crown having teeth and a thickness greater than the thickness of said blade head base so that a kerf cut by said teeth is of sufficient width to accommodate the distal end of said blade bar; and at least one drive rod that is connected to said blade head and extends from said blade head base towards the proximal end of said blade bar and that is configured for releasable attachment to said drive member of said saw oscillating drive assembly so that the actuation of said drive member results in reciprocation of said at least one drive which results in the oscillation of said blade head.

7. The sagittal saw and blade cartridge assembly of claim 6, wherein, said at least one rib of said blade cartridge does not extend forward of the distal end of the saw head.

8. The surgical saw and blade cartridge assembly of claim 6, where said blade cartridge is formed so that said at least one rib extends outwardly away from said blade bar so that when said blade cartridge is mounted to said saw, said at least one rib extends outwardly away from the saw head surface.

9. The surgical saw and blade cartridge assembly of claim 6, wherein said blade cartridge is formed so that the at least one said rib is two said ribs and said ribs are located on opposed sides of said blade bar so that when said blade bar is seated on the surface of said saw head, said ribs are located on opposed sides of said clamping member of said saw clamping assembly.

10. The surgical saw and blade cartridge assembly of claim 6, wherein said blade cartridge is further constructed so that the at least one said drive rod is two said drive rods.

11. The surgical saw and blade cartridge assembly of claim 6, wherein said blade bar is formed to have at least one second opening located distal to the proximal end of said blade bar and proximal to the first opening in said blade bar, where said blade cartridge at least one drive rod engages said drive member of said saw oscillating drive assembly through the at least one second opening; and said blade cartridge is formed so that said at least one rib extends distally forward from a location on said blade bar distal to the at least second opening and proximal to the first opening.

12. A sagittal saw and blade cartridge assembly, including:

a saw having:

a head with a surface, said saw head having a distal end;

a lock assembly attached to said saw head, said lock assembly including a coupling component configured to move towards and away from the surface of said saw head, said coupling component being mounted to said saw head so as to be spaced proximally from the distal end of said saw head; and an oscillating drive assembly mounted to said head that has a drive member shaped to engage at least one blade cartridge drive rod, the oscillating drive assembly configured to receive a rotational movement and convert the rotational movement into movement that oscillates the drive member; and a blade cartridge including:

a blade bar that has a base and a distal end opposite the base, the blade bar base being configured to seat on the surface of said saw head and below said coupling component so that movement of said coupling component towards the surface of said saw head presses said coupling component against said blade bar to releasably hold said blade bar to said saw head, said blade bar being further shaped to have at least one rib that extends outwardly from an outer surface of said blade bar, said at least one rib being located on the base of said blade bar so as to extend over a portion of said blade bar that is seated on the surface of said saw head wherein, when said blade bar is seated on the surface of said saw head, said at least one rib extends distally away from said coupling component and has an end that is spaced proximally away from the distal end of said blade bar;

a blade head, said blade head having: a base disposed in said blade bar adjacent the distal end of said blade bar; and a crown that extends forward from said blade head base so as to be located forward of the distal end of said blade bar, said crown having teeth and having a thickness greater than that of said blade head base, said teeth having a thickness so that a kerf cut by said teeth is of sufficient width to accommodate said blade bar; and at least one drive rod that is connected to said blade head base and that extends from said blade head base towards the proximal end of the blade bar, said drive rod configured for releasable attachment to said drive member of said saw oscillating drive assembly so that the oscillation of said drive member results in reciprocation of said at least one drive rod which results in the oscillation of said blade head.

13. The sagittal saw and blade cartridge assembly of claim 12, wherein, said at least one rib of said blade cartridge does not extend forward of the distal end of said saw head.

14. The surgical saw and blade cartridge assembly of claim 12, wherein:
   said saw head is further formed to have a proximal end and said coupling component of said lock assembly is mounted to said saw head so as to be spaced distally from the proximal end of said saw head; and
   said blade cartridge at least one rib is located on the base of said blade bar so as to extend proximally away from said coupling component of said lock assembly.

15. The surgical saw and blade cartridge assembly of claim 12, where said blade cartridge is formed so that said at least one rib extends outwardly away from said blade bar so that when said blade cartridge is mounted to said saw, said at least one rib extends outwardly away from the saw head surface.

16. The surgical saw and blade cartridge assembly of claim 12, wherein:
   said saw head has a proximal end;
   said clamping component of said lock assembly is mounted to said saw head so as to be located distally forward of the proximal end of said saw head; and
   said at least one rib of said blade bar of said blade cartridge extends distally forward along said blade bar from a location located distal to a proximal end said blade bar, past said clamping component and does not extend forward of the distal end of said saw head.

17. The sagittal saw and blade cartridge assembly of claim 12, wherein, said blade cartridge is further formed so that:
   said blade bar base forms a proximal end of said blade bar;
   an opening is formed in said blade bar, said opening being located distally forward of the proximal end of said blade bar and being positioned so that, when said blade bar is seated on the surface of said saw head, said coupling component extends through said opening; and
   said blade bar is further formed so that said at least one rib extends both proximally rearward from and distally forward from the opening in said blade bar.

18. The surgical saw and blade cartridge assembly of claim 12, wherein said blade cartridge is further constructed so that:
   said at least one rib extends distally forward of said coupling component of said lock assembly;
   said blade head base is disposed in said blade bar to pivot around a static surface internal to said blade bar; and
   said at least one drive rod is two said drives internal to said blade bar is two said drive rods, wherein said drive rods are connected to said blade head base and extend proximally from said blade head base on opposed sides of the static surface internal to said blade bar around which said blade head base pivots.

19. A sagittal saw and blade cartridge assembly, including:
   a saw having:
      a head with proximal and distal ends and a surface;
      a lock assembly attached to said saw head, said lock assembly including a coupling component configured to move towards and away from the surface of said head, said coupling component being mounted to said saw head so as to be spaced distally forward from the proximal end of said saw head;
      an oscillating drive assembly mounted to said head that has a drive member shaped to engage at least one blade cartridge drive rod, said oscillating drive assembly configured to receive a rotational movement and convert the rotational movement into movement that oscillates the drive member; and
   a blade cartridge including:
      a blade bar that has a base and a distal end opposite the base, the blade bar base being configured to seat on the surface of said saw head and below said coupling component so that movement of said coupling component towards the surface of said saw head presses said coupling component against the base of said blade bar to releasably hold said blade bar to said saw head, said blade bar being further shaped to have at least one rib that extends outwardly from an outer surface of said blade bar, said rib being located on the base of said blade bar so as to extend over a portion of said blade bar that is seated on the surface of said saw head, wherein said at least one rib extends proximally away from said coupling component and has an end that is spaced proximally away from the distal end of said blade bar;
      a blade head, said blade head having a base disposed in said blade bar adjacent the distal end of said blade bar and a crown that extends forward from said base so as to be located forward of the distal end of said blade bar, said crown having teeth and having a thickness greater than that of said blade head base, said teeth having a thickness so that a kerf cut by said teeth is of sufficient width to accommodate said blade bar; and
      at least one drive rod that is connected to said blade head base and that extends from said blade head base towards the proximal end of said blade bar, said drive rod configured for releasable attachment to said drive member of said saw oscillating drive assembly so that the oscillation of said drive member results in reciprocation of said at least one drive rod which results in the oscillation of said blade head.

20. The sagittal saw and blade cartridge assembly of claim 19, wherein said blade bar is further formed so that, when said blade bar is seated on the surface of said saw head, said at least one rib extends both proximally rearward and distally forward of said coupling component of said lock assembly.

21. The sagittal saw and blade cartridge assembly of claim 19, wherein said blade bar is further formed so that, when said blade bar is seated on the surface of said saw head, said at least one rib extends both proximally rearward and distally forward of said coupling component of said lock assembly and said at least one rib does not extend distally forward of the distal end of said saw head.

22. The surgical saw and blade cartridge assembly of claim 19, where said blade cartridge is formed so that said at least one rib extends outwardly away from said blade bar so that when said blade cartridge is mounted to said saw, said at least one rib extends outwardly away from the saw head surface.

23. A sagittal saw and blade cartridge assembly, including:
   a saw having:
      a head having proximal and distal ends and a surface;
      a lock assembly that includes a clamping member mounted to said saw head that extends over the saw head surface at a location proximal to the distal end of said saw head and that is moveably mounted to said saw head so as to selectively bear against a bar disposed on the saw head surface so as to secure the bar to the surface; and an oscillating drive assembly mounted to said head that has a drive member shaped to engage at least one blade cartridge drive rod, said oscillating drive assembly configured to receive a rotational moment and convert the rotational moment into movement that oscillates the drive member; and a blade cartridge including:
  a blade bar that has opposed proximal and distal ends, a length between the ends and that is releasably seated on the surface of said saw head so as to be disposed between the surface and said lock assembly clamping member so that the clamping member can releasably hold said blade bar to the saw head surface, said blade bar being formed with at least one first opening located distal to the proximal end of said blade bar and second opening located distally forward of the at least one first opening through which, when said blade bar is seated on the surface of said head, said clamping member extends;
  at least one rib that extends outwardly from an outer surface of said blade bar, said rib extending distally forward from a location on said blade bar that is distal to the at least one first opening in the blade bar and proximal to the second opening in said blade bar and that extends a distance along said blade bar that is less than one-half the length of said blade bar so as to terminate at a location proximal to the distal end of said blade bar;
  a blade head having a base disposed in said blade bar adjacent the distal end and a crown that extends forward from said base so as to be located forward of the distal end of said blade bar, said crown having teeth and a thickness greater than the thickness of said blade head base so that a kerf cut by said teeth is of sufficient width to accommodate the distal end of said blade bar; and
  at least one drive rod that is connected to said blade head base and extends from said blade head base to the at least one first opening in said bar and that is configured for releasable attachment through the at least one first opening in said blade bar to said drive member of said saw oscillating drive assembly so that the actuation of said drive member results in reciprocation of said at least one drive which results in the oscillation of said blade head.

24. The sagittal saw and blade cartridge assembly of claim 23, wherein, said at least one rib of said blade cartridge does not extend forward of the distal end of the saw head.

25. The surgical saw and blade cartridge assembly of claim 23, where said blade cartridge is formed so that said at least one rib extends outwardly away from said blade bar so that when said blade cartridge is mounted to said saw, said at least one rib extends outwardly away from the saw head surface.

26. The surgical saw and blade cartridge assembly of claim 23, wherein said blade cartridge is formed so that the at least one said rib is two said ribs and said ribs are located on opposed sides of the second opening in said blade bar.

27. The surgical saw and blade cartridge assembly of claim 23, wherein said blade cartridge is further constructed so that:
  said at least one rib extends distally forward of the second opening is said blade bar;
  said blade head base is disposed in said blade bar to pivot around a static surface internal to said blade bar; and
  said at least one drive rod is two said drives internal to said blade bar is two said drive rods, wherein said drive rods are connected to said blade head base and extend proximally from said blade head base on opposed sides of the static surface internal to said blade bar around which said blade head base pivots.

* * * * *